(12) United States Patent
Palafox

(10) Patent No.: US 11,904,252 B1
(45) Date of Patent: Feb. 20, 2024

(54) THERAPEUTIC DEVICE

(71) Applicant: Savanna Palafox, Buckeye, AZ (US)

(72) Inventor: Savanna Palafox, Buckeye, AZ (US)

( * ) Notice: Subject to any disclaimer, the term of this patent is extended or adjusted under 35 U.S.C. 154(b) by 76 days.

(21) Appl. No.: 17/349,503

(22) Filed: Jun. 16, 2021

Related U.S. Application Data

(60) Provisional application No. 63/043,458, filed on Jun. 24, 2020.

(51) Int. Cl.
| | | |
|---|---|---|
| *A63H 3/02* | (2006.01) | |
| *A61M 21/02* | (2006.01) | |
| *A63H 3/00* | (2006.01) | |
| *A63H 3/28* | (2006.01) | |
| *A61M 21/00* | (2006.01) | |

(52) U.S. Cl.
CPC ............ *A63H 3/003* (2013.01); *A61M 21/02* (2013.01); *A63H 3/02* (2013.01); *A63H 3/28* (2013.01); *A61M 2021/0022* (2013.01); *A61M 2021/0027* (2013.01)

(58) Field of Classification Search
CPC .......... A63H 3/00; A63H 3/003; A63H 3/005; A63H 3/02; A63H 3/28; A63H 3/36; A61M 21/02; A61M 2021/0022; A61M 2021/0027
USPC ............ 446/71, 73, 268, 297, 369, 385, 397
See application file for complete search history.

(56) References Cited

U.S. PATENT DOCUMENTS

| | | | | |
|---|---|---|---|---|
| 5,456,626 A | * | 10/1995 | Ming-Kang | ............ B05B 11/00 222/39 |
| 6,012,963 A | * | 1/2000 | Lee | .......................... A63H 3/36 428/905 |
| 6,520,826 B2 | * | 2/2003 | Spector | .................. A63H 3/001 446/72 |
| 6,749,479 B2 | * | 6/2004 | Vick | ........................ A63H 3/02 446/72 |
| 6,786,792 B2 | * | 9/2004 | Ritchey | .................... A63H 3/02 446/76 |
| 6,800,015 B1 | * | 10/2004 | Derges | .................... A61L 9/042 239/211 |
| 6,805,607 B2 | * | 10/2004 | Hidalgo | ................... A63H 3/02 446/369 |
| 6,940,432 B1 | * | 9/2005 | Hall | ....................... A63H 3/003 341/110 |

(Continued)

FOREIGN PATENT DOCUMENTS

KR    20110051699    11/2019

*Primary Examiner* — Alexander R Niconovich
(74) *Attorney, Agent, or Firm* — David Colls; Berger Singerman LLP

(57) ABSTRACT

A therapeutic device shaped like a stuffed animal device that generally includes an outer casing and an inner casing. The outer casing defines an external structure configured to resemble an animal, such as a body having a head, a torso, and at least one pair of limbs each having a leg and a foot. The inner casing is located in the torso. The inner casing is configured with multiple contiguous weighted chambers each holding a collection of micro-glass beads. An audio playback device is disposed in the head. Each foot includes a weighted container carrying a portion of micro-glass beads. A fill material or stuffing is disposed in the head and in the torso about the inner casing. The fill material is also disposed in the leg and in the foot about the weighted container. Textured features are applied to the ears and to the bottom side of the feet.

18 Claims, 10 Drawing Sheets

(56) References Cited

U.S. PATENT DOCUMENTS

| | | | | |
|---|---|---|---|---|
| 7,169,008 B2* | 1/2007 | Ritchey | A01K 15/025 446/76 |
| 8,230,630 B2* | 7/2012 | Storch | H04R 1/028 40/717 |
| 9,089,782 B2* | 7/2015 | Achan, Jr. | A63H 3/003 |
| 9,327,094 B2* | 5/2016 | Patel | A63H 3/28 |
| 9,914,062 B1* | 3/2018 | Jiencke | G09B 17/006 |
| 11,213,761 B2* | 1/2022 | Lyell | A63H 3/001 |
| 11,324,848 B2* | 5/2022 | Roszell | A61L 9/014 |
| 11,577,044 B2* | 2/2023 | Parisien | A63H 3/28 |
| 2005/0101220 A1* | 5/2005 | Jackson | A63H 3/02 446/369 |
| 2006/0222560 A1* | 10/2006 | Stanley, III | A61L 9/12 422/5 |
| 2007/0042672 A1* | 2/2007 | Tawil | A63H 3/02 446/369 |
| 2007/0054593 A1* | 3/2007 | Santos | G09B 1/02 446/369 |
| 2008/0302308 A1* | 12/2008 | Supino | A63H 3/005 119/174 |
| 2011/0097967 A1* | 4/2011 | Berrymon | A63H 13/02 446/321 |
| 2012/0028532 A1* | 2/2012 | Thompson | A63H 3/02 446/73 |
| 2012/0145091 A1* | 6/2012 | Wang | A01K 15/026 264/45.3 |
| 2013/0017756 A1* | 1/2013 | Lai | A01K 15/025 446/369 |
| 2013/0217301 A1* | 8/2013 | Cote | A63H 9/00 446/490 |
| 2014/0357154 A1* | 12/2014 | Richmond | A63H 37/00 446/397 |
| 2016/0158112 A1* | 6/2016 | Summers | A63H 3/02 446/73 |
| 2016/0158658 A1* | 6/2016 | Lakritz | A63H 33/006 446/268 |
| 2017/0028304 A1* | 2/2017 | Stray | A63H 3/005 |
| 2017/0113151 A1* | 4/2017 | Smith | A63H 3/02 |
| 2017/0151504 A1* | 6/2017 | Villano | A61J 17/02 |
| 2017/0157280 A1* | 6/2017 | Young | A61L 9/14 |
| 2018/0078866 A1* | 3/2018 | Rogone | A61J 17/1111 |
| 2019/0125915 A1* | 5/2019 | Roszell | A61L 9/12 |
| 2019/0160683 A1* | 5/2019 | Hayashi | B25J 19/023 |
| 2019/0224444 A1* | 7/2019 | Kalensky | A63H 3/28 |
| 2022/0054796 A1* | 2/2022 | McGreevy | A61M 21/02 |
| 2022/0323305 A1* | 10/2022 | Benezri | A63H 3/02 |

\* cited by examiner

THERAPEUTIC DEVICE

CROSS-REFERENCE TO RELATED APPLICATIONS

This application claims the benefit of U.S. Provisional Patent Application Ser. No. 63/043,458, filed Jun. 24, 2020, which is hereby incorporated by reference herein in its entirety.

FIELD OF THE INVENTION

The present invention relates generally to therapeutic articles, and more particularly, to a therapeutic liftable device shaped like an animal toy that incorporates a variety of features that promote therapeutic effects for kids and adults suffering from all forms of autism, trauma, mental health.

BACKGROUND OF THE INVENTION

Although therapy is not always necessary for the improvement of someone's mental health, it can be extremely helpful in many cases. Some individuals do not realize they need help, since they perceive therapy as something to be sought after only if experiencing crippling mental illness. However, therapy may be useful for anyone, especially if they experienced recent life challenges like family struggles, divorce, or the death of a loved one. The effects of these experiences differ depending on the individual and may not be debilitating, but most are negatively impacted by them for a long period of time and could benefit from therapy.

In 2018, statistics by the National Alliance on Mental Health (NAMI) showed that one out of every five American adults live with a mental health condition, while one in twenty-five adults live with a serious mental health condition. From the adults who fall within the first of the two categories, only 40% of them seek help. There are many reasons behind the refusal to seek help for mental illness. The stigma that is associated with mental health treatment may lead judgment from close friends and family members, inciting shame and embarrassment. Further, the lack of understanding of when you should seek therapy may be a deterrent, since many people do not know what warrants therapy. Additionally, fully recovering from a mental health disorder often requires a lot of time and energy to be channeled into therapy.

Substantial research shows that young adults (ages 18-25) have the highest chance of developing mental illness compared to any other age group. In fact, another statistic by the aforementioned NAMI indicates that 50% of all lifetime mental illness begins by age 14, and 75% by age 24. Although this trend has persisted for decades, it has seen a significant increase with the rise in popularity of social media, which many researchers have pointed to as the main source of problem. Social media not only keeps individuals from interacting face-to-face, but also serves as a platform in which cyber-bullying is rampant and rarely controlled. This, coupled with the fact that the transition from adolescence to adulthood is a period of vulnerability and fragility, creates the perfect recipe for development of lasting mental illness.

There are many different types of therapy, but one that is referred to most often is psychotherapy. During psychotherapy, the patient sits across a licensed mental health care professional and talks about the topics that surround the source of the patient's weakened mental health. The objective of these therapy sessions is for the patient to discover what is triggering their illness and to devise healthy coping mechanisms. Although effective, this option is expensive and not available to many who need it. According to the World Health Organization, an overwhelming majority of people with mental and psychosocial disabilities are living in poverty, poor physical health, and are subject to human rights violations. Populations from these disadvantaged backgrounds also see a higher prevalence of trauma, autism, ADHD, and other mental disabilities. In order to make therapy more accessible to everyone, digital therapeutics have gained popularity, but has its own restrictions. According to NAMI, digital therapeutics should be considered a tool rather than a treatment of mental illness, since it fails to provide any significant improvements by itself. The problem with digital therapy is that it relies on virtual interactions with others, making them impersonal and lacks the important face-to-face interaction previously mentioned. Further, a phone with access to these applications is not affordable to the population most affected by mental illness.

Therefore, there is an unmet need to promote mental health treatment options to patients in demographics that are suffering from mental illnesses, emotional imbalances, disabilities such as, PTSD, Down syndrome, Autism, and other disorders and traumas. These treatment options must involve some form of real interaction, be affordable such that everyone has a chance to participate and improve, and ease the symptoms of mental illnesses ranging from ADHD and autism in children to dementia in the elderly, and other traumas or disabilities.

SUMMARY OF THE INVENTION

The present invention, in one form, is directed to a therapeutic device that incorporates a variety of components offering different stimulus features that promote therapy-inducing responses. An outer casing is configured in the form of an animal. An inner casing is disposed within the body of the animal and contains features to promote a tactile, auditory, and olfactory stimulus. The inner casing extends through the torso of the animal body and at least partially through the neck. The overall appearance of the animal presents a visual stimulus. An external feature such as an animal collar is configured to deliver an independent olfactory stimulus. The animal feet are configured to deliver a tactile stimulus. A collection of weighted beads, such as micro-glass beads in one exemplary form, is disposed within the inner casing and the animal feet to provide the tactile stimulus feature. An audio device installed in the inner casing provides an auditory stimulus. An internal aromatic diffuser (such as wool saturated with essential oils) disposed within the inner casing provides an olfactory stimulus. Certain anatomical locations are furnished with suitable stuffing material to add a tactile enhancement, such as in the head and feet. A pair of zippers provided at the outer casing and inner casing enable access into the interior of the device.

The present invention, in another form, is directed to a therapeutic stuffed article. In one embodiment, the stuffed article may comprise a boy or girl stuffed figure. Alternatively, in another exemplary embodiment, the therapeutic stuffed article may comprise an animal. As shown in the exemplary drawings, the article is shaped like a stuffed animal toy that generally includes an outer layer or casing and an inner casing or enclosure. The outer casing defines an external structure configured to resemble, for example, an animal, an anthropomorphic figure, a creature, or a character. The animal may be configured as one of a biped and a quadruped figure. The outer casing forms a body having a head, a torso, and at least one pair of limbs each having a leg and a foot. The inner enclosure is located at an interior portion of the body in the torso. The inner enclosure is configured with multiple contiguous weighted chambers each holding a collection of micro-glass beads to provide the weighting feature. An audio playback device is disposed in the head. Each foot includes a weighted container carrying a portion of micro-glass beads. A fill material or stuffing is disposed in the head and in the torso about the inner casing. The fill material is also disposed in the leg and in the foot about the weighted container. An enclosure may be provided in each limb to hold and otherwise contain the foot combination comprising the weighted container and the surrounding fill material. Textured features are applied to the ears and to the bottom side of the feet. A zipper may be provided in the neck of the body to permit access into the interior of the body, such as to remove and/or replace the audio device.

Introducing a first embodiment of the invention, the present invention consists of a therapeutic device, comprising:

an exterior portion and an interior portion;
the exterior portion including an outer casing defining a body;
the interior portion including an intermediary casing and an inner casing disposed at least in part within a torso and a neck of the body, a first gap existing between the intermediary casing and the outer casing,
a plurality of spherical objects; and
wherein an audio device and an aromatic diffuser element are disposed between the first gap, and
wherein the inner casing carries a first portion of the spherical objects in a loose distribution arrangement.

In a second aspect, the spherical objects include micro-glass beads.

In another aspect, a second gap exists between the intermediary casing and the inner casing.

In another aspect, stuffing material is disposed within the second gap.

In another aspect, the body includes a head filled with stuffing material.

In another aspect, the body includes a set of legs having feet filled with a mixture of stuffing and a second portion of the spherical objects.

In another aspect, the device includes an aromatic collar disposed about a neck of the body.

In another aspect, the device includes a layer of stuffing disposed at least partly within a clearance space between the outer casing and the inner casing.

In another aspect, the exterior portion conforms to the figure of an animal.

In yet another aspect, the outer casing is furnished with a zipper.

Introducing a second embodiment of the invention, the present invention consists of a therapeutic liftable device, comprising:

a body having a head, a torso, and at least two limbs;
an outer structure defining an exterior of the body;
a plurality of objects;
an inner enclosure disposed in the torso and including a plurality of compartments each containing a respective portion of the objects; and
a fill material, wherein a respective portion of the fill material is disposed in the head and wherein a respective portion of the fill material is disposed in the torso about the inner enclosure.

In another aspect, at least one of the at least two limbs respectively includes a leg and a foot. The foot includes a combination and an enclosure carrying the combination. The combination comprises a container containing a respective portion of the objects and further comprises a respective portion of the fill material disposed about the container. A respective portion of the fill material is disposed in the leg.

In another aspect, each object includes a micro-glass article.

In another aspect, the device includes a removable audio playback device disposed in the head.

In another aspect, the body is configured in the shape of at least one of an anthropomorphic figure, an animal, a character, or a creature. Additionally, the body may be configured as one of a biped and a quadruped animal figure.

In another aspect, the device includes a removable user-activatable audio device disposed in the head; an accessway defined in the outer structure and configured to enable access into an interior of the body; a pair of ears disposed on the head; and, a first textured feature defined in at least one side of at least one ear. Additionally, at least one of the at least two limbs respectively includes a leg and a foot. The foot includes a combination and an enclosure carrying the combination. The combination comprises a container containing a respective portion of the objects and further comprises a respective portion of the fill material disposed about the container. A respective portion of the fill material is disposed in the leg. A second textured feature is defined at a bottom side of the foot.

In another aspect, each foot or a selected foot of the respective device may include a covering that covers the foot to prevent the textured features on the foot from making unintentional contact with other elements, such as skin, hair, or clothing. The covering is attached to the top portion of the foot and folded over, covering the entire foot to have a seamless foot matching the other feet of the device.

In another aspect, the accessway is located proximal a neck of the body. The accessway may include a zipper.

In yet another aspect, the outer structure includes a first portion encompassing the head and torso and a second portion distinct from the first portion and encompassing the at least two limbs.

In still another aspect, the device includes a clearance gap between the inner enclosure and the outer structure. The clearance gap contains fill material.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a stuffed device shaped like an animal toy that incorporates various features that are tailored to produce therapeutic effects in a user, such as a child or other individual experiencing, mental health, emotional and/or psychological distress. The therapeutic features offer a range of stimulus, which interact with the user at several sensory levels, including auditory, tactile, olfactory, and visual that work in combination to lessen anxiety, and provide comfort during some physical or psychological episodes.

Figure 1:
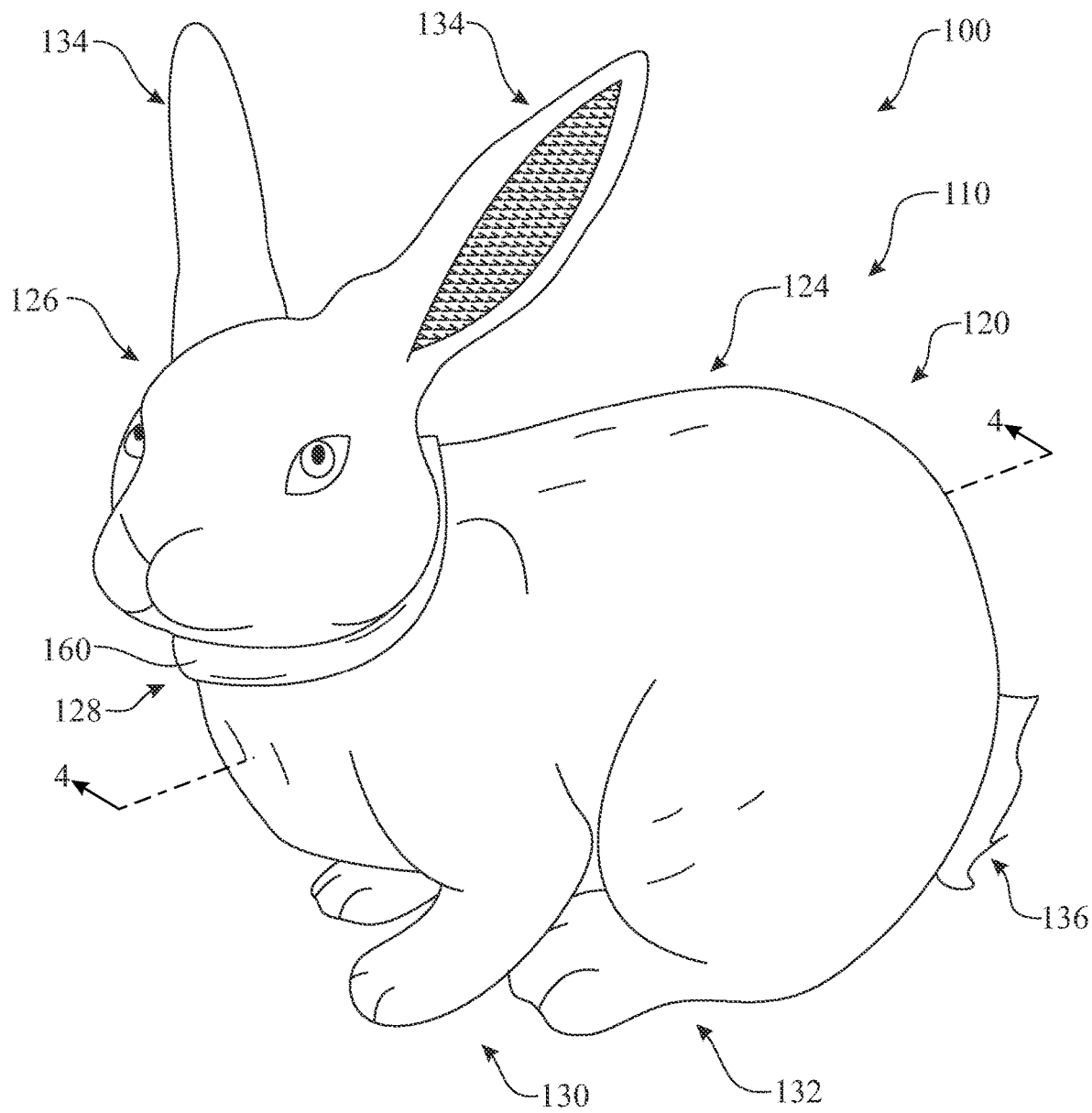
FIG. 1 presents an anterior, lateral perspective view showing a first embodiment of the therapeutic stuffed animal device of the present invention.
Figure 2:
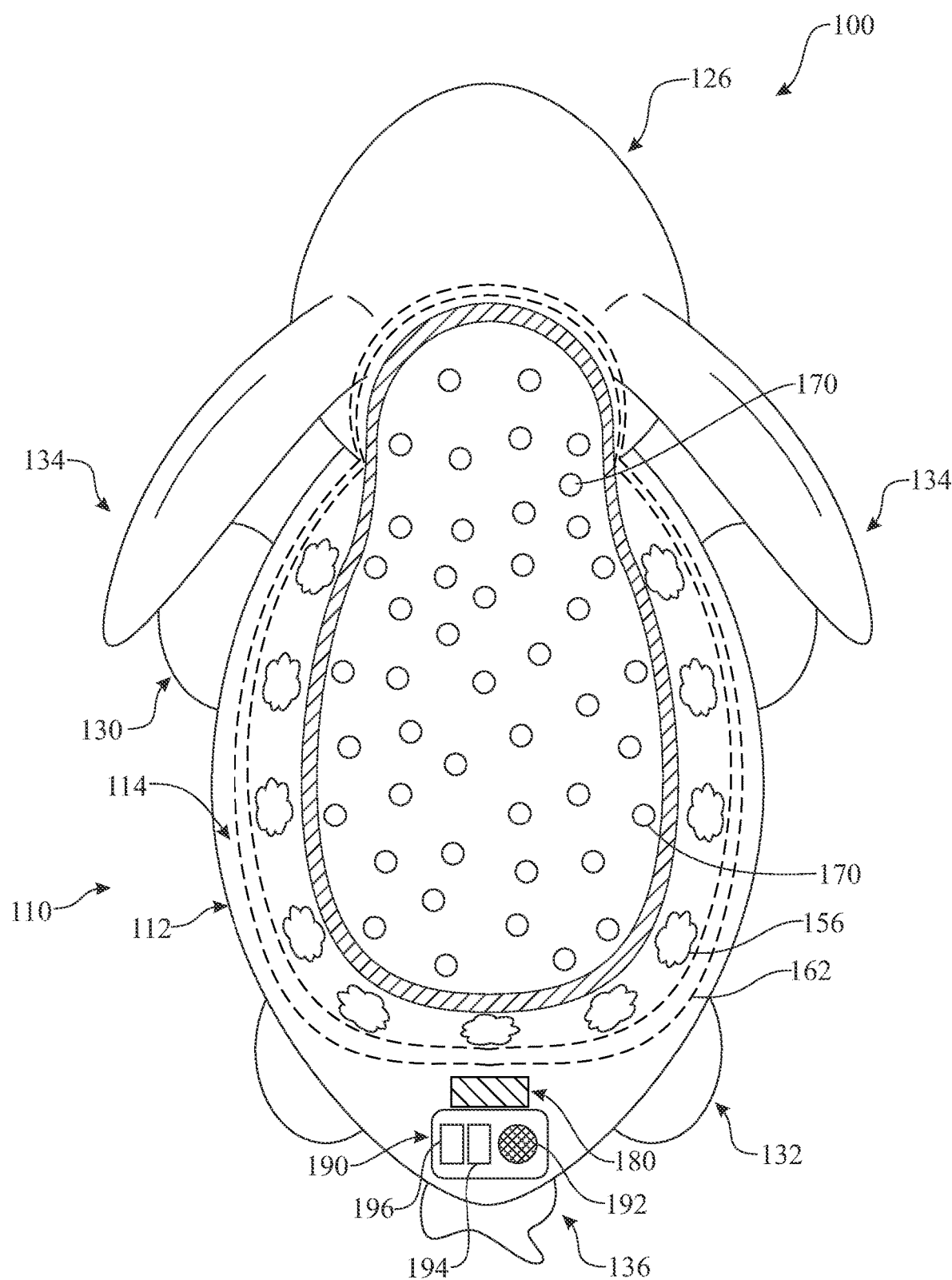
FIG. 2 presents a dorsal-side, diagrammatic, upper plan interior view of the first embodiment of the therapeutic stuffed animal device of the present invention, illustrating the longitudinal relationship among various interior features located inside the innermost body lining of the stuffed animal device.
Figure 3:
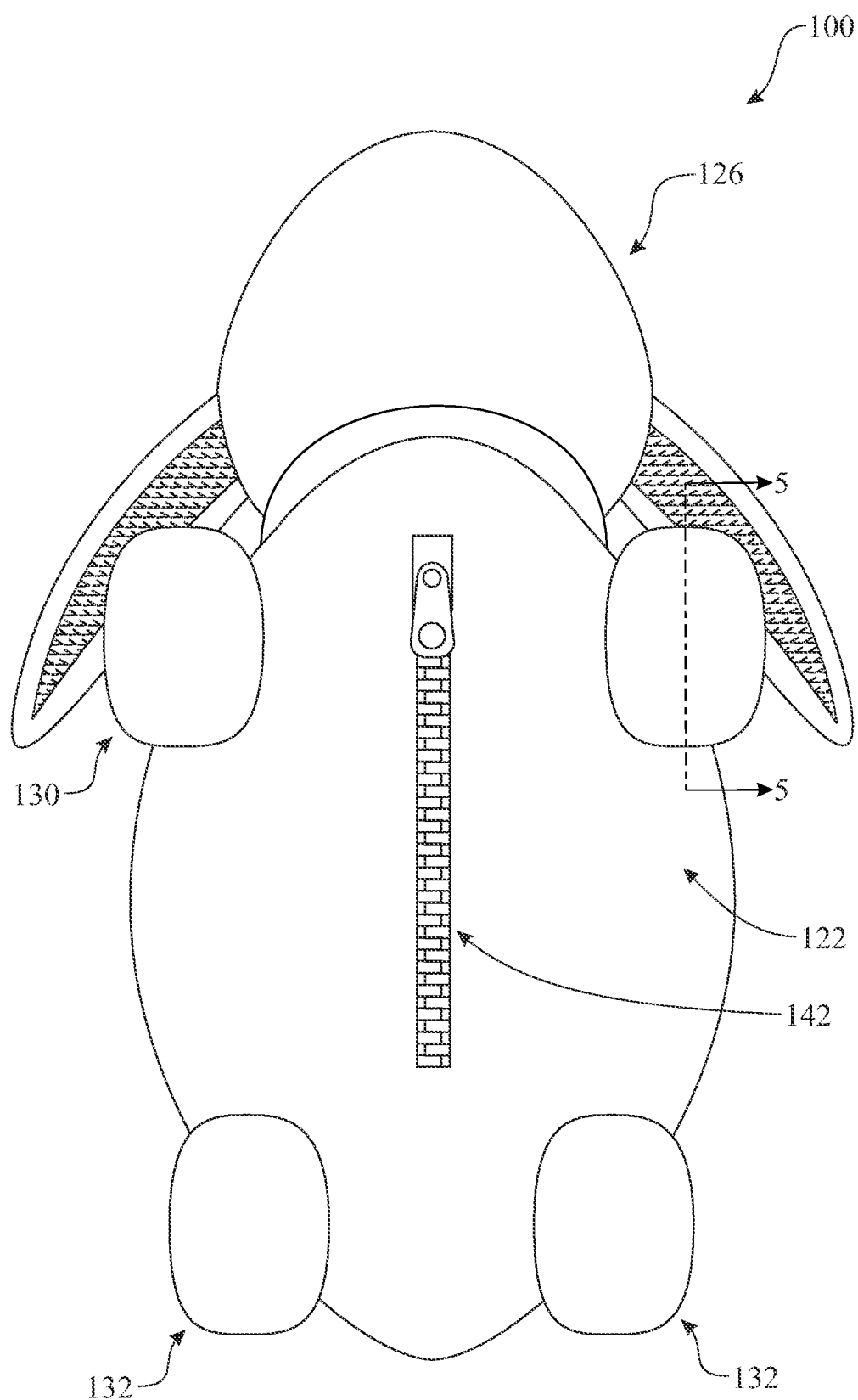
FIG. 3 presents a ventral-side, bottom elevation view of the first embodiment of the therapeutic stuffed animal device of the present invention, illustrating the location of a zipper adapted to facilitate access to the interior of the stuffed animal.
Figure 4:
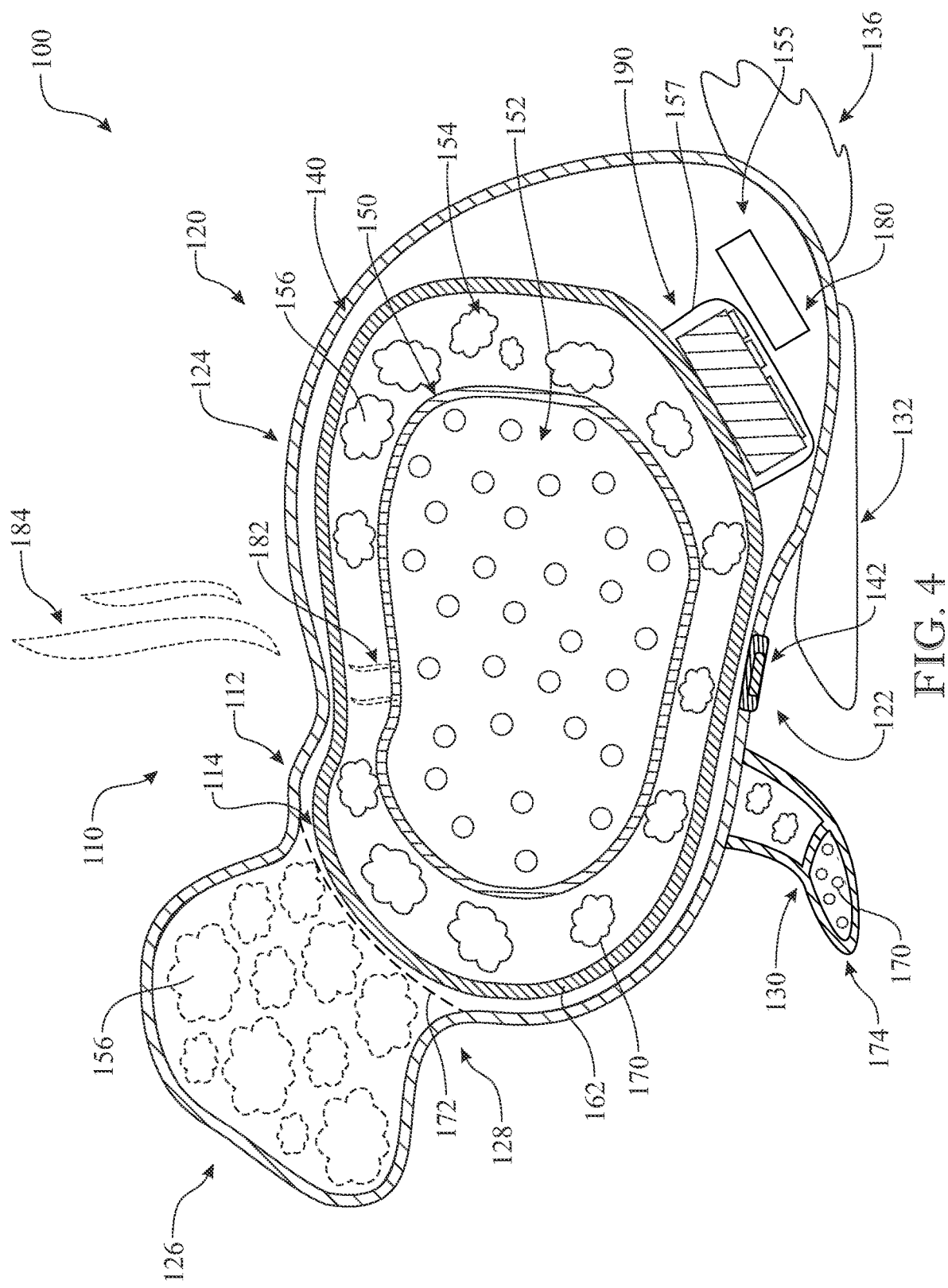
FIG. 4 presents a median cross-sectional diagrammatic view of the first embodiment of the therapeutic stuffed animal device of the present invention, taken along lines 4-4 of FIG. 1, illustrating the spatial arrangement among various interior features located inside the innermost body lining of the stuffed animal device.

Referring initially to FIGS. 1, 2 and 4, a stuffed device in the shape of an animal toy 100 is disclosed, according to a first embodiment of the present invention. The device 100 can be configured as any suitable article or figure, including an animal (real or fictional depiction), a figure resembling a character (e.g., cartoon or literary), a creature (real or fictional depiction), or some other appropriate animate or inanimate object. In alternate forms, the stuffed animal device 100 is configured as a rabbit (as depicted in FIGS. 1-7), a pig, or a dog (not presently shown). The depiction of device 100 as a rabbit in FIGS. 1-6 is merely illustrative and should not be considered in limitation of the present invention, as device 100 can be rendered in a variety of other forms that likewise incorporate the various functional features disclosed in FIGS. 1-6. Generally, in preferred forms, the animal depicted by device 100 will be anatomically accurate, both in terms of structural features and proportion, as a way to enhance the realism of device 100. However, this preferential construction should not be considered in limitation of the present invention, as other versions are possible incorporating exaggerated, supplemental, or misplaced features.

The device 100 includes a body 110 having an exterior portion generally illustrated at 112 and an interior portion generally illustrated at 114 that defines an interior body space or cavity encompassed by exterior portion 112. The combination of exterior portion 112 and interior portion 114 cooperatively defines the shape and structure of an animal, such as the depicted rabbit. In a form resembling the anatomy of a rabbit, the body 110 includes a torso 120 including a belly 122 and a back 124, a head 126, a neck 128, a pair of forelegs 130, and a pair of hindlegs 132.

The exterior portion 112 of body 110 includes an external shell, lining or outer casing 140 that is sized, shaped, and dimensioned to form the structural anatomy of the desired creature, such as the illustrated rabbit. In a manner befitting a toy rabbit, the outer casing 140 includes an outer skin that is formed from a suitable material composition such as a layer of fur, which forms the outermost section of device 100. The outer casing 140 is preferably made of a suitable permeable or semi-permeable material, membrane or fabric that permits aromatic smells originating from the interior body portion 114 to diffuse and otherwise communicate through outer casing 140 into the ambient environment outside device 100 (as discussed further), where the emitted smell is sensed by a user handling device 100. The outer casing 140 is configured with a zipper 142 (FIG. 3) provided at the belly 122 of body 110 to permit a user to access the interior body portion 114. In a preferred exemplary embodiment, the head 126 of the body 110 may be closed off or sewn internally 172 to prevent access to the interior portion of the head 126.

With continued reference to FIGS. 2 and 4, the body 110 further includes an inner lining or casing 150 disposed at the interior portion 114 of body 110, and an intermediary casing 162 disposed between the inner casing 150 and the outer casing 140 of body 110. The inner casing 150 defines a closed sac or pouch having an interior space or hollow 152. In one form, the intermediary casing 162 occupies and extends through a space at the interior body portion 114 that includes the torso 120 and at least a portion of neck 128 (FIG. 4). A gap or clearance space 154 is defined between inner casing 150 and intermediary casing 162 that preferably spans at least the full expanse of torso 120. In one form, the clearance or spatial separation defined by gap 154 is maintained by filling gap 154 with a suitable amount of material such as wool stuffing, which is flexible yet sufficiently dense when appropriately packed to maintain the spacing between inner casing 150 and outer casing 140. The interior space of head 126 is also packed or filled with stuffing 156. The outer casing 140 is preferably configured with a zipper 142 to permit a user to access the gap 155 between the intermediary casing 162 and the outer casing 140.

A combination of therapeutic features are integrated with inners casings. Briefly, in overview, an array of small objects (round glass beads or micro beads) 170 are disposed in scattered, distributed form throughout the interior space 152 of inner casing 150, presenting both tactile stimulus feature and weight for deep pressure therapy. An aromatic diffuser element 180 located within the gap 155 between the intermediary casing 162 and the outer casing 140. The diffuser 180 is configured to emit a fragrant odor, providing an olfactory stimulus. An acoustic or audio device 190 is located within the same gap 155. The audio device 190 transmits a therapeutically favorable sound, offering an auditory stimulus. The audio device 190 and/or the diffuser 189 in one exemplary embodiment can be disposed inside of a pouch 157, such as a drawstring pouch, that is attached to the exterior of the intermediary casing 162.

Referring particularly to FIGS. 2 and 4, the interior space 152 of inner casing 150 is filled with a collection of solid, spherical, objects or balls 170. In one form, solid balls 170 are made of solid, micro-glass beads. The glass beads 170 are distributed randomly throughout the interior space 152 of inner casing 150. The packing density of glass beads 170 within inner casing 150 can be appropriately selected to achieve the desired auditory and sensory effect. The glass beads 170 serve various sensory functions in terms of delivering tactile stimuli and auditory stimuli. For example, when a user handles, squeezes, or otherwise manipulates device 100, especially around the region of torso 120 of animal body 110, the interaction and contact between glass beads 170 generates an auditory stimulus heard by the user. The sound emitted by the contact between glass beads 170 is amenable to generating a therapeutic effect for individuals experiencing severe auditory sensitivities. Additionally, from a tactile perspective, the glass beads 170 collectively present a weighted pressure-applying stimulus to a user holding device 100, which produces a therapeutic effect on an individual who experiences a distress-reducing sensitivity in response to physical interactions (e.g., reductions in emotional distress such as anxiety and stress commensurate with tactile experiences). In a preferred form, the interior space 152 of inner casing or lining 150 is stuffing-free, namely, the void within inner casing 150 is substantially filled with micro-glass beads 170 as content (packing) material.

In one form, the device 100 is configured to promote a suitable weighting characteristic amenable to Deep Pressure Therapy (DPT), of which the glass beads 170 are one component to support such DPT effects. In terms of a somatic or physical constitution that is configured to deliver multiple tactile stimuli, the body 110 of device 100 has a multi-layered or multi-leveled construction. An outer casing 140 defines the general peripheral contour or shape of device 100 (e.g., illustrated rabbit) and is preferably supplied with an exposed fur layer directly contactable by a user. The outer casing 140 defines an interior space 114 of device 100. An inner casing 150 is filled at its interior space 152 with glass beads 170 and disposed at the interior space 114 of outer casing 140, forming a weighted, pressure-inducing layer. A wool stuffing layer is disposed in-between intermediate casing 162 and inner casing 150 at clearance space 154, where wool stuffing material is inserted as fill material. The intermediate layer of wool stuffing at clearance gap 154 provides a soft, cushioning feature that buffers any undue external impact of glass beads 170 contained in inner casing 150, yet is sufficiently thin to transmit the hard, firm, marbled feel of the glass beads 170 to someone holding and manipulating device 100.

This multi-level or multi-sectioned arrangement of device 100 offers various stimulus features. The fur layer at the exterior of outer casing 140 has a pleasant texture providing a soft, cuddling effect. Additionally, the fur layer, adapted to the figure depicted by device 100 (e.g., rabbit), constitutes a visual stimulus and thereby provides a visually appealing and soothing effect. The wool layer 140 offers a supple, cushion-type tactile engagement. One will appreciate that alternative materials, such as polyester or the like, can be utilized in lieu of wool (or in combination) without departing from the scope of the invention. The glass beads 170, contained at the innermost section in inner casing 150, offer both weight for deep pressure therapy and tactile stimuli. The even distribution of glass beads 170 throughout inner casing 150, and the extension of inner casing 150 throughout the main area of body 110 (torso 120 and at least part of neck 128), provides overall balance to device 100 and allows a user to experience the weighted, pressure-bearing effect of glass beads 170 at most carrying positions of device 100, without too much weight isolated in one place. In this way, the weight characteristic of device 100 resembles that of the actual animal which device 100 is meant to depict. This even distribution compares favorably to other versions that contain the beads in the base (e.g., belly area) or in a more densely packed bag for weighting purposes. In a preferred form, there are no glass beads 170 in head 126, ears 134, and tail 136, though these body parts are preferably filled with wool stuffing. The contact or collision between individual glass beads 170 do not produce an acoustic quality discernible by the user. The glass beads 170 are pre-measured to a specific weight to provide adequate weight for deep pressure therapy (DPT). The beads are dense and their texture is smooth to reduce or altogether eliminate any discernable noise that would otherwise agitate individuals that are sensitive to acoustic sounds.

Referring still to FIGS. 2 and 4, device 100 includes an aromatic diffuser element 180 that is integrated within the body 110, according to another therapeutic feature of the present invention. The diffuser element 180 functions to emit a therapeutically pleasant odor 182 that wafts omni-directionally within the interior gap 155, eventually emerging externally from device 100 as ambient fragrant odor 184 due to the odor-permeability of outer casing 140. The ambient fragrant odor 184 operates as an olfactory stimulus to a user holding device 100, who will sense (smell) the odor 184. In a preferred form, the aromatic diffuser element 180 will maintain a constant discharge or emission of odor 182. The aromatic diffuser element 180 may be implemented with a wool material to take advantage of the aroma retention properties of wool. For example, prior to installation, a wool article is suffuse or saturated with a fragrant substance, such as essential oils. The aromatic emissions from diffuser element 180 are preserved due to the quality of wool to hold a fragrance. Any suitable location of aromatic diffuser element 180 is possible, but one appropriate position locates element 180 at a generally central location within body torso 120.

Figure 6:
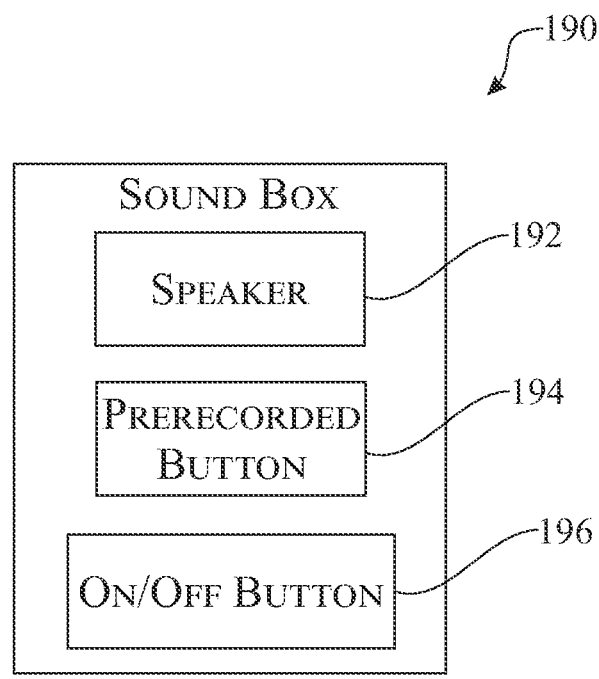
FIG. 6 presents a block diagram schematic view of the first embodiment of the therapeutic stuffed animal device of the present invention, illustrating the various electrical components used to construct the acoustic feature incorporated into the stuffed animal device.
Figure 7:
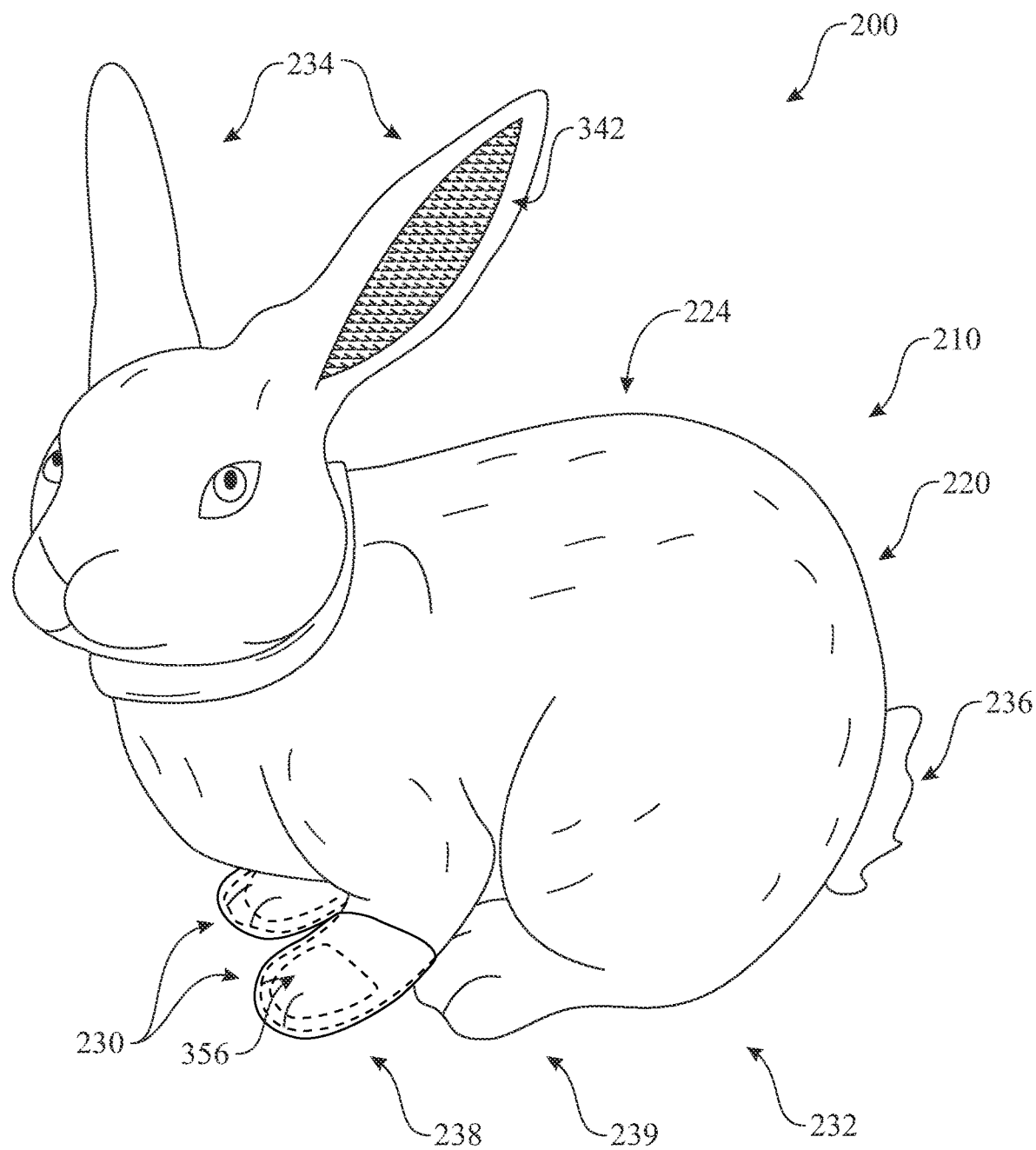
FIG. 7 presents an anterior, lateral perspective view showing a second embodiment of the therapeutic stuffed animal device of the present invention, illustrating a set of coverings for the front feet.

Referring still to FIGS. 2 and 4, in addition to FIG. 6, an audio device 190 is located within the device body 110, according to another therapeutic feature of the present invention. The audio device 190 functions to selectively produce a pre-recorded sound program. In one form, audio device 190 is provided in the form of a removable soundbox programmed with a specified duration of pre-recorded bells (e.g., twenty-five minutes). Any suitable sound material, however, can be programmed for playback in audio device 190. The selection of audio material preferably is designed to promote therapeutic effects in the listener. A program of pre-recorded bells, for example, may have a rhythmic coordination with biological features of the user. In one form, the chiming of the bells may be synchronized to the respiration of the listener (e.g., child playing with device 100), which promotes proper breathing practices in the user and aids in restoring balance to the nervous system through its effect on the autonomic nervous system. Additionally, a proper selection of audio material (e.g., purely non-lyrical) may serve as a calming tool in relation to coping with forms of emotional, somatic and psychological distress, such as anxiety, sleep issues, trauma, and the alleviation of post-traumatic stress disorder (PTSD) symptoms. Any suitable location of audio device 190 is possible, but one appropriate position locates device 190 at a generally posterior end and lower side (towards belly 122) of body torso 120.

For ease of operation and selective user control, the audio device 190 is provided with a set of manual controls, such as the combination of on/off switch 196 and play button 194. The audio device 190 is preferably disposed at a location suitable for activation of the controls, such as at a lower section of body 110. In one form, for example, placement of audio device 190 proximate to belly 122 enables the user to reach the selection features 194, 196 (indirectly) by probing through gap 155, provided between the outer casing 140 and intermediary casing 162, until reaching the control selectors on audio device 190. Alternately, the operating selection features 194, 196 can be reached directly by first opening zipper 142 attached to outer casing 140 (FIG. 3) at the underside of belly 122 to access interior portion 114, and then by accessing the interior gap 155 and reaching the audio device inside of pouch 157 that is attached to the exterior of the intermediary casing 162 where audio device 190 is located. The parent of a child who is utilizing the device 100, for example, can perform this access procedure. The audio device 190 is furnished with a built-in speaker 192. The audio device 190 is a stand-alone unit powered, for example, by suitable childproof and child-safe batteries.

Device 100 is provided with various aromatic features, located both inside and outside the device animal 100, which are designed to convey a scented stimulus to the olfactory senses (smell organs) of an individual handling device 100, according to aspects of the invention. First, as discussed above, a wool diffuser 180 is located inside the device animal 100, within the interior gap 155 between the intermediary casing 162 and the outer casing 140. Second, as illustrated in FIG. 1, device 100 is provided with a removable, aromatic, smell-emitting diffuser collar 160 disposed about neck 128. The collar 160 incorporates a scented material or substance that continuously emits a fragrant smell that is bio-compatible with favorable human sensitivity. The fragrant emissions are detectable by someone holding, or in near proximity to, device 100. The fragrant emissions from collar 160 facilitate a therapeutic effect such as aromatherapy, in which exposure to such fragrant smells is conducive to positive outcomes regarding physical and emotional treatment protocols. In one form, collar 160 is made of wool that carries a fragrant substance, such as essential oils. Preferably, the collar 160 is pure (100/6) wool. However, other suitable fabric blends (natural and synthetic) are possible. This choice of fabrication for collar 160 takes advantage of the feature that pure wool has a high aroma retention property and is suitable for aroma-therapeutic finish applications. Various alternatives are possible with the type of aroma diffused by collar 160, but preferably the choice will support an aroma-type therapeutic effect. The olfactory stimulus provided by collar 160 can be adjusted by removing and installing a different collar.

Figure 5:
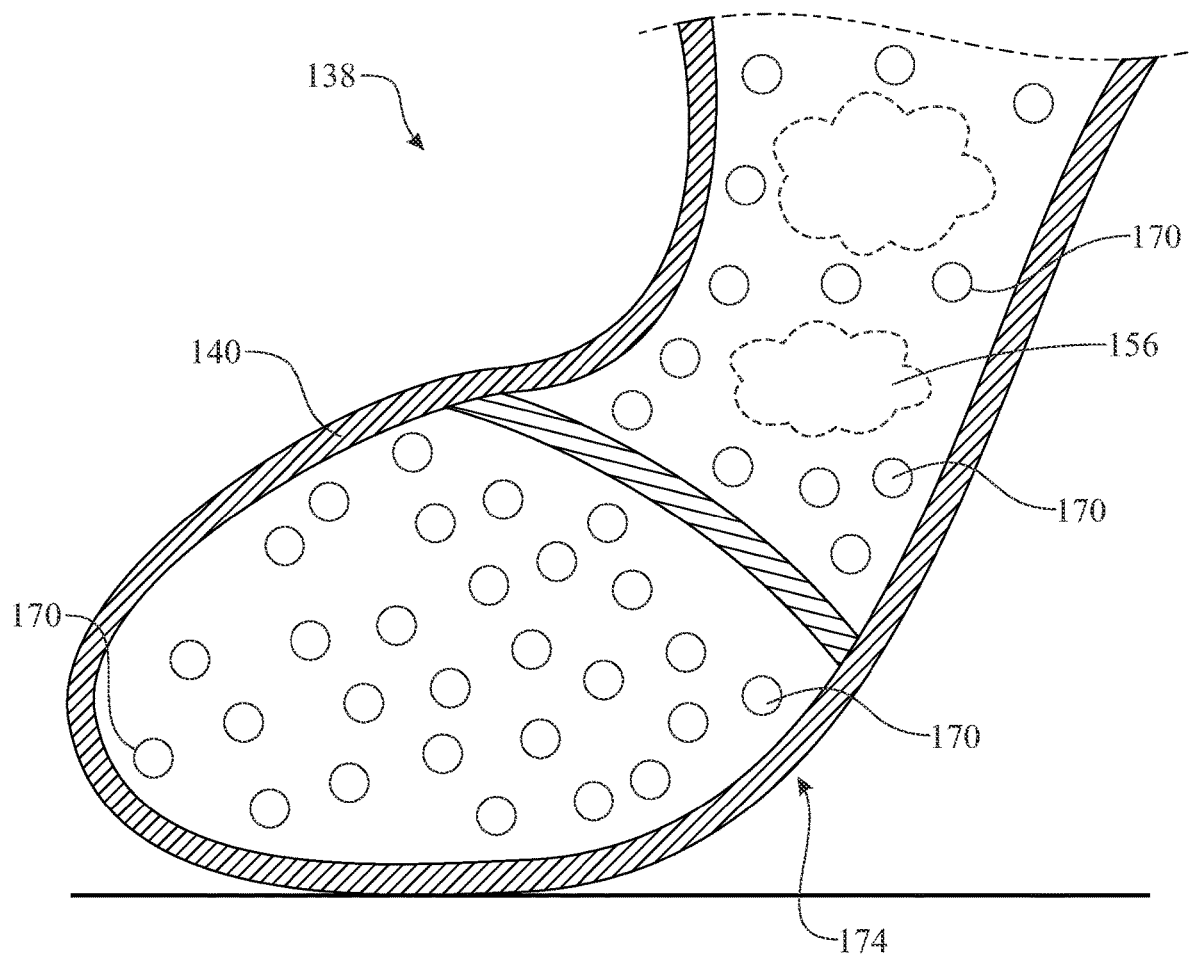
FIG. 5 presents an expanded, fragmented, median cross-sectional view of the first embodiment of the therapeutic stuffed animal device of the present invention, taken along lines 5-5 of FIG. 3, illustrating the interior features located inside one of the front feet.

Referring now to FIGS. 4 and 5, the foot or paw 138 of forelegs 130 and hindlegs 132 (FIG. 1) is filled with a distributed mixture of micro-glass beads 170 and stuffing 156. The device 100 includes a weighted pair of forelegs 130, and a pair of hindlegs 132. Each pair of forelegs 130 and hindlegs 132 may include stuffing 156 and/or beads 170 about the limbs of each leg. Each forefoot and hindfoot, however, includes a sac or pouch 174 filed with weighted beads 170 (or glass beads) that are sewn and sealed off from the remaining interior gaps and content inside of the body 110 of the device 100. The forefoot and hindfoot can then be used as a stress ball for therapeutic relief purposes. The packing density of beads 170 and stuffing 156 is tailored to create a suitable stress and anxiety-relieving functionality, similar to the effect produced by engagement with stress balls. The combination of beads 170 and stuffing 156 offers both an auditory and tactile stimulus, in response to a user interacting with device 100, namely, by squeezing or grasping the rabbit foot 138. Although other suitable ball-type objects may be employed, the use of micro-glass beads 170 has several benefits. The glass beads 170 have a white sand texture and a finish that is perfectly smooth, making them a very suitable alternative to conventional objects having the texture of plastic poly pellets. The glass beads 170 are particularly helpful for individuals with severe auditory and sensory sensitivities, due to the pleasant tactile stimulation afforded by glass beads 170 and the favorable sound produced by their interaction as device 100 is manipulated. Moreover, glass beads 170 are environmentally and sensory-friendly. Any suitable silica material can be used to implement beads 170.

Referring to FIGS. 1 and 3, the ears 134 may have any suitable texture to facilitate a desired tactile stimulus. In one form, ears 134 will have a roughened texture compatible with a tactile stimulus found to provide relief from psychological distress (such as self-harm and anxiety) when the user engages the stimulus. The principle behind such a stimulus-response patterns is that interaction with this type of stimulus can promote a response known as grounding (bringing attentional focus to the present) that serves to detour or distract from dispositions towards self-harm or to ease restlessness. For this purpose, ears 134 can be made of a material having a texture such as a polyester Velcro hook (i.e., the rough side of Velcro).

In one exemplary form, the outer casing 140 of the device 100 is preferably configured and otherwise constructed to be machine washable and machine dryable. In the instance case, the outer casing is removed, exposing the other internal contents located inside of the device (which are retained inside of the intermediary casing 162), and washed. After the covering is washed and dried, the covering is reinstalled or otherwise disposed over the internal contents of the device. In another exemplary embodiment, the audio device and diffuser are removed from the insides of the device body and the device, as a whole (i.e., the outer cover and all of the internal elements such as the wool, glass beads, etc.), is machine-washed and machine-dried. The materials for making device 100 are preferably hypoallergenic, non-toxic, and free of substances such as BPAs, phthalates, and latex. The zipper 142 provided on outer casing 140 is preferably childproof to hinder removal of contents from device 100. The concentration of wool stuffing in the spacing 154 between outer lining or casing 140 and intermediary casing 162 limits the fallout of stuffing material when gap 155 is accessed, such as to remove audio device 190 or diffuser 180. The set of legs 130, 132 preferably have a closed stitching feature. In terms of construction, any suitable arrangement can be utilized to build device 100. For example, a main integral body section can be defined by outer casing 140 as a single unit or shell, with various appendages attached to it at the anatomically appropriate locations (e.g., tail 136, legs 130, 132, and ears 134).

Device 100 is configured with the ability to renew or replace various functional features. Some of the components contained within the device body 110 can be renewed or replaced as needed or desired. In a preferred embodiment, a user can first access the interior portion 114 of device 100 by unzipping zipper 142 at outer casing 140 to access the inner contents inside of the device body 110. This access might be desired to renew the internal aromatic diffuser 180 (i.e., replenish it with essential oils), to reprogram audio device 190 (i.e., substitute a new recording for the one already installed), or remove the diffuser 180 and audio device 190 altogether to machine wash the device 100. The available removal and replacement of these components highlights the adaptability of device 100. In another less desirable form, yet plausible example, the inner casing 150 with the glass beads and other components such as, the diffuser 180, stuffing 156, and audio device 190 may be considered a replaceable package or unit that can be substituted for another one. This modular feature enables device 100 to be adaptable to the particular needs and sensitivities of the user, such as specific fragrances and sounds that offer a personalized therapeutic system tailored to the individual. The outer casing 140 is also replaceable to provide different covering options with varying colors.

Device 100 offers a diverse array of therapeutic components. The appearance of exterior portion 112 of device body 110 offers a visual stimulus, made all the more pleasing and conducive to distress relief by its resemblance to an appealing figure (such as an animal or other mood-enhancing character). The texture of exterior body portion 112 presents a tactile stimulus. The ears 134 may be enhanced with a roughened texture that offers a corresponding tactile stimulus. The aroma emitted by the removable aromatic collar 160 and the internal aromatic diffuser located inside of the device body 110 function as therapeutic components presenting an olfactory stimulus. The operation of audio device 190 delivers a planned auditory stimulus. Again, the glass beads 170 offer a tactile stimulus and deep pressure therapy as the user manipulates device 100 and senses the physical properties of glass beads 170 (e.g., hardness, miniature size, shifting weight). In some embodiments, the device will weight approximately four to about six pounds.

Referring now to FIGS. 7-10, a therapeutic stuffed device in the shape of an animal device 200 is disclosed, according to a second embodiment of the present invention. Similar features and components between the first embodiment disclosed in FIGS. 1-6 and the second embodiment disclosed in FIGS. 7-10 are indicated by the same reference numeral except the leading digit is changed from a '1' (FIGS. 1-6) to a '2' (FIGS. 7-10). The device 200 includes a body 210 having an exterior portion generally illustrated at 212 in the form of a lining, casing, shell or outer layer that forms an enclosure or closed interior portion generally illustrated at 214. The animal device 200, in a preferred form, is configured in the shape of an animal, such as the illustrated rabbit, which is anatomically complete and accurate with generally proportionate features. For animal representations, the device figure can be a biped or quadruped. Other implementations may include, without limitation, an American Bully dog, an *iguana*, a macaw, an alpaca, a baby goat, a Munchkin cat, and a turtle. It should be apparent to those skilled in the art that exterior portion 212 of device body 210 can be readily provided in a form or configuration that resembles a desired animal, creature, character, or other such figure.

In rabbit form, body 210 includes a torso 220 having a lower, ventral side or belly generally illustrated at 222 and an upper, dorsal side or back generally illustrated at 224. A tail 236 extends from torso 220. The body 210 further includes a head 226 having a pair of ears 234. A neck generally illustrated at 228 connects the head 226 to the torso 220. The body 210 further includes a pair of forelimbs or forelegs generally illustrated at 230 and a pair of hindlimbs or hindlegs generally illustrated at 232. The forelegs 232 are equipped with a pair of front feet or paws 238, while the hindlegs 232 are similarly equipped with a pair of rear feet or paws 239. In rabbit form, the interior portion 214 of body 210 includes an inner torso space or cavity generally illustrated at 216 and an inner head space or cavity generally illustrated at 218. In one form, the inner torso cavity 216 communicates directly and is contiguous with inner head cavity 218. In an alternate form, a divider or partition may be located at the neck region 228 of body 210 to establish a boundary between inner head cavity 218 and inner torso cavity 216.

Figure 9:
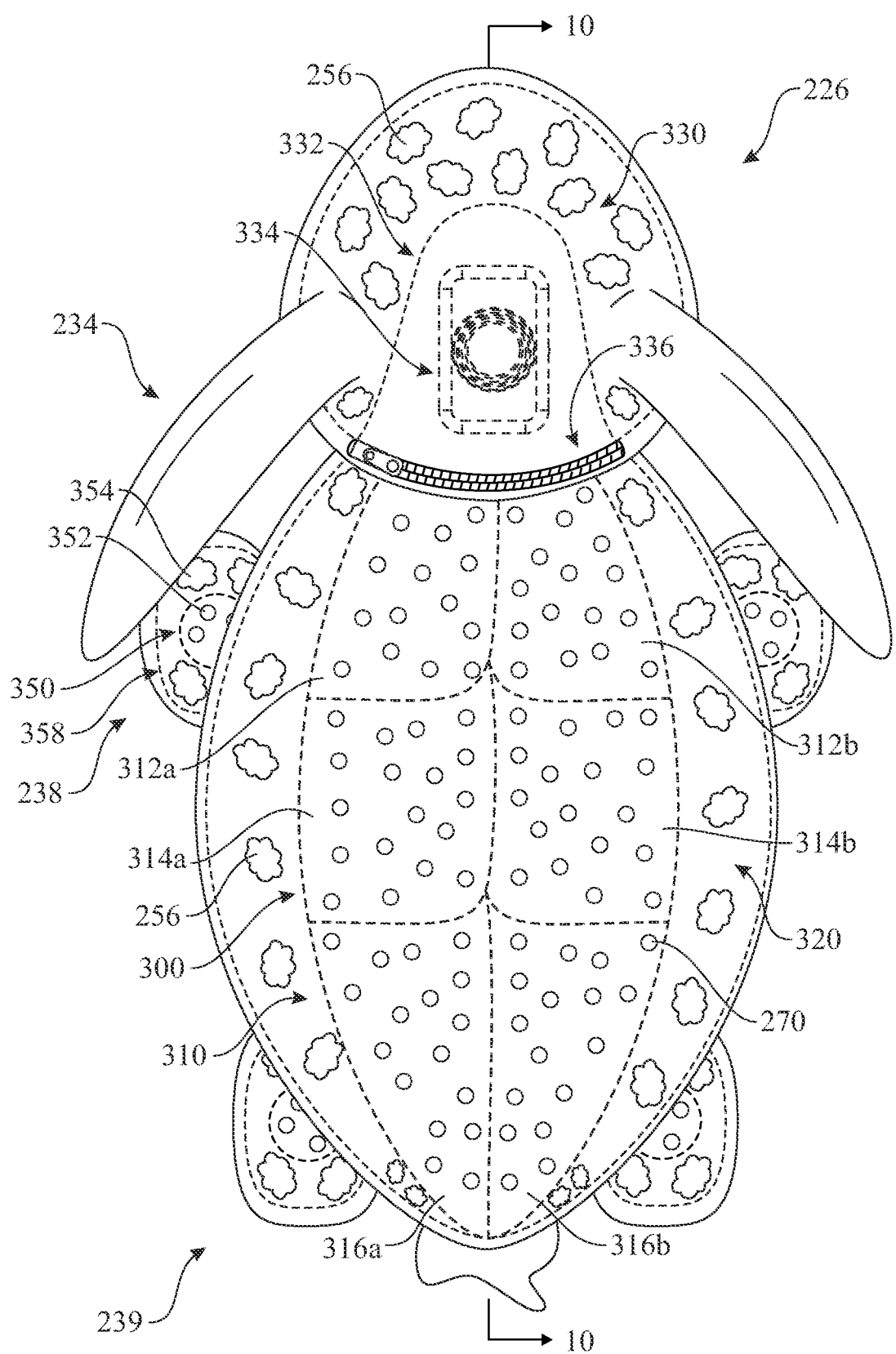
FIG. 9 presents a dorsal-side, partial interior upper view of the second embodiment of the therapeutic stuffed animal device of the present invention, illustrating internal features of the head, body, and feet.
Figure 10:
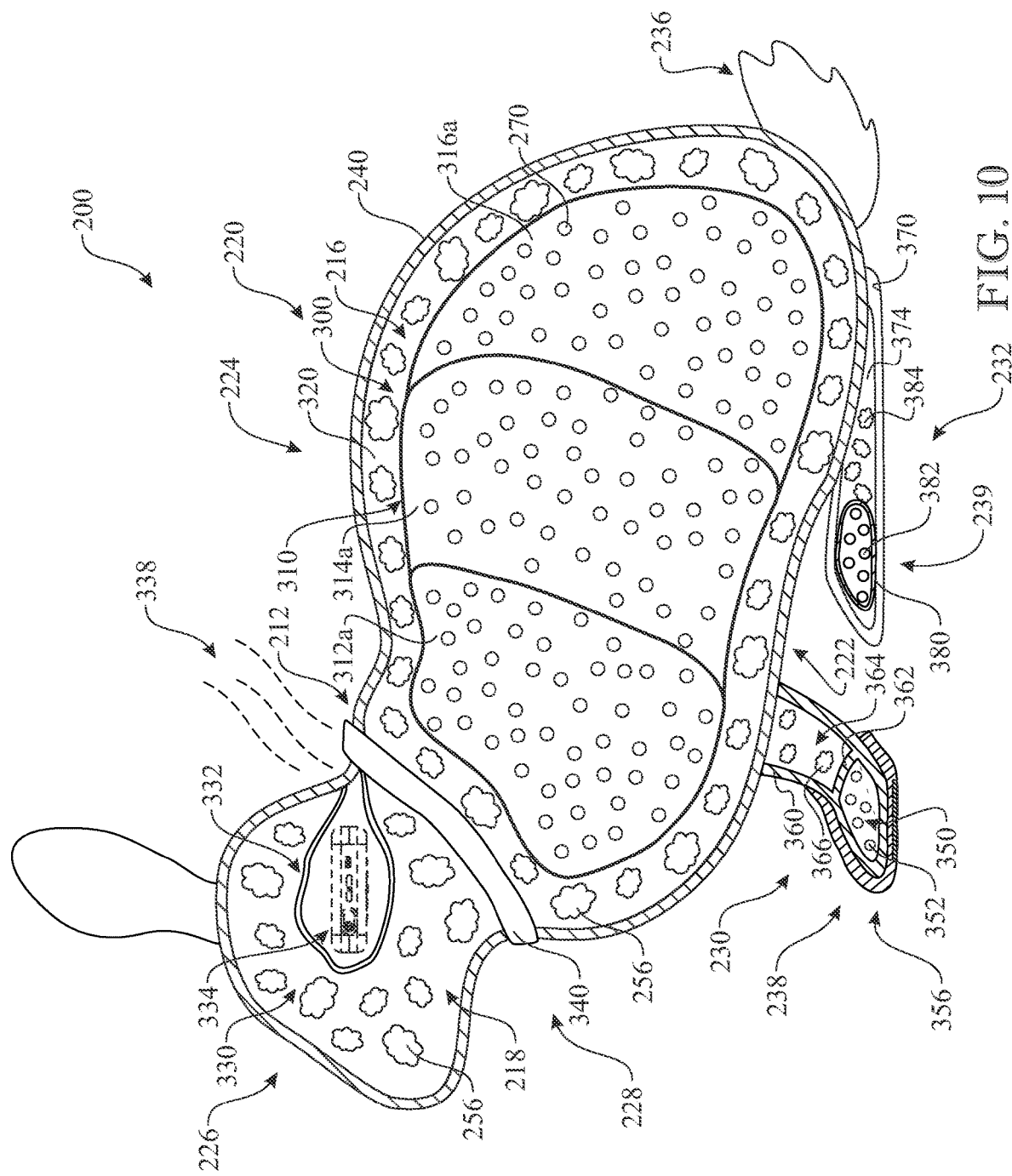
FIG. 10 presents a median cross-sectional diagrammatic view of the second embodiment of the therapeutic stuffed animal device of the present invention, taken along lines 10-10 of FIG. 9.

Referring more particularly to FIGS. 9 and 10, torso 220 is configured as a multi-layered structure including outer layering feature 240, inner layering feature 300, and intermediate layering feature 320 interposed between 240 and 300. The exterior portion 212 of body 210 is defined by an outer fur layer 240 shaped into the desired figure (rabbit) and having an appearance or resemblance to the animal. In one form, the outer fur layer 240 is contiguous and without discontinuities to prevent access into the interior portion 214 of body 210 via the outer fur layer 240. Optionally, access into body 210 may be facilitated with the use of a neck zipper 336 preferably located peripherally about neck 228. The inner layering feature 300 is configured as a bead-filled, weighted layer and provided in the form of a flexible, inner core enclosure or sack 300. The inner core enclosure 300 includes a lining or casing 310 constructed or organized into a multi-chamber, multi-compartment arrangement. In one illustrative form, the inner casing 310 includes a pair of laterally adjacent front chambers 312a,b; a pair of laterally adjacent intermediate chambers 314a,b; and, a pair of laterally adjacent rear chambers 316a,b. The casing 310 is suitably positioned inside torso 220 so that the boundary between the first set of same-side chambers 312a, 314a, and 316a and the second set of same-side chambers 312b, 314b, and 316b is generally aligned along a midline or median of animal device 200 to create a bilateral symmetry. Each chamber of casing 310 is filled or loaded with a suitable collection of micro-glass beads 270 to created a weighted formation. Each chamber is closed so that the contents cannot escape. The bilateral, symmetrical location of bead-filled casing 310 within torso 220 provides an even distribution of pressure when someone is holding device 200. The weighted feature of device 200 facilitates the communication of a deep pressure therapeutic experience to an individual holding device 200. The intermediate layering feature 320 is defined by a gap, interstitial area, or clearance space 320 defined between outer fur layer 240 and inner casing 310. The intermediate clearance space 320 is filled with a suitable amount of stuffing material 256 to surround inner casing 310 and stably locate inner casing 310 in a bilateral symmetrical position within torso 220. The stuffing material 256 may include any suitable substance, such as Perfect Loft® 100% polyester cluster fiber fill, for example. The stuffing material 256 promotes a soft, cuddly effect, and, fills-out the volume of animal device 200. In one formation, torso 220 of body 210 may be regarded as a configuration having outer fur layer 240, inner weighted layer 300, and intermediate filling layer 320. The multi-chamber inner casing 310 is suitably sized and shaped so that the inner casing 310, when filled with beads 270, extends substantially the longitudinal dimension of torso 220 and occupies a desired volume of torso 220.

The head 226 of body 210 is equipped with an audio assembly 330 that includes, in combination, an audio player or device such as a sound box 334 and a pouch or carrier 332 that holds and otherwise contains audio player 334. The combination of carrier 332 and audio player 334 is disposed within the inner cavity space 218 of head 226. The audio player 334 includes pre-recorded audio content that can be played back using any suitable control mechanism, such as a wireless control or a push-button control that can be accessed by adequately depressing the head section of outer layer 240 at the appropriate location until engagement is made with the push-button control. The emitted sound 338 from audio player 334 can be heard in a proximal vicinity or neighborhood exterior to device 200, particularly by an individual holding device 200. The stored audio content of audio player 334 is preferably tailored to promote a therapeutic effect on the listener. The head 226 is filled with an adequate amount of stuffing material 256 to appropriately shape and contour head 226. The audio assembly 330 can be accessed, as needed (e.g., for replacement purposes), by entry through childproof neck zipper 336. Illustrative dimensions for sound box 334 may be 2" width, 2" length, 1" depth. As an optional feature, the neck 228 may be fitted with a collar 340.

The ears 234 have a textured feature 342 formed at their underside. The textured feature 342, for example, may be provided in the form of a polyester Velcro hook (i.e., the rough side of Velcro). The ears 234 may be provided in any of various configurations. In one form, for example, the ears 234 have a stiff bendable feature that avoids a flopping behavior and enables ears 234 to stand up and be bent at any of various points to create a temporary, reversible angled orientation. As an optional feature, the ears 234 may be provided with a removable set of covers, similar to a mitten flap.

Figure 8:
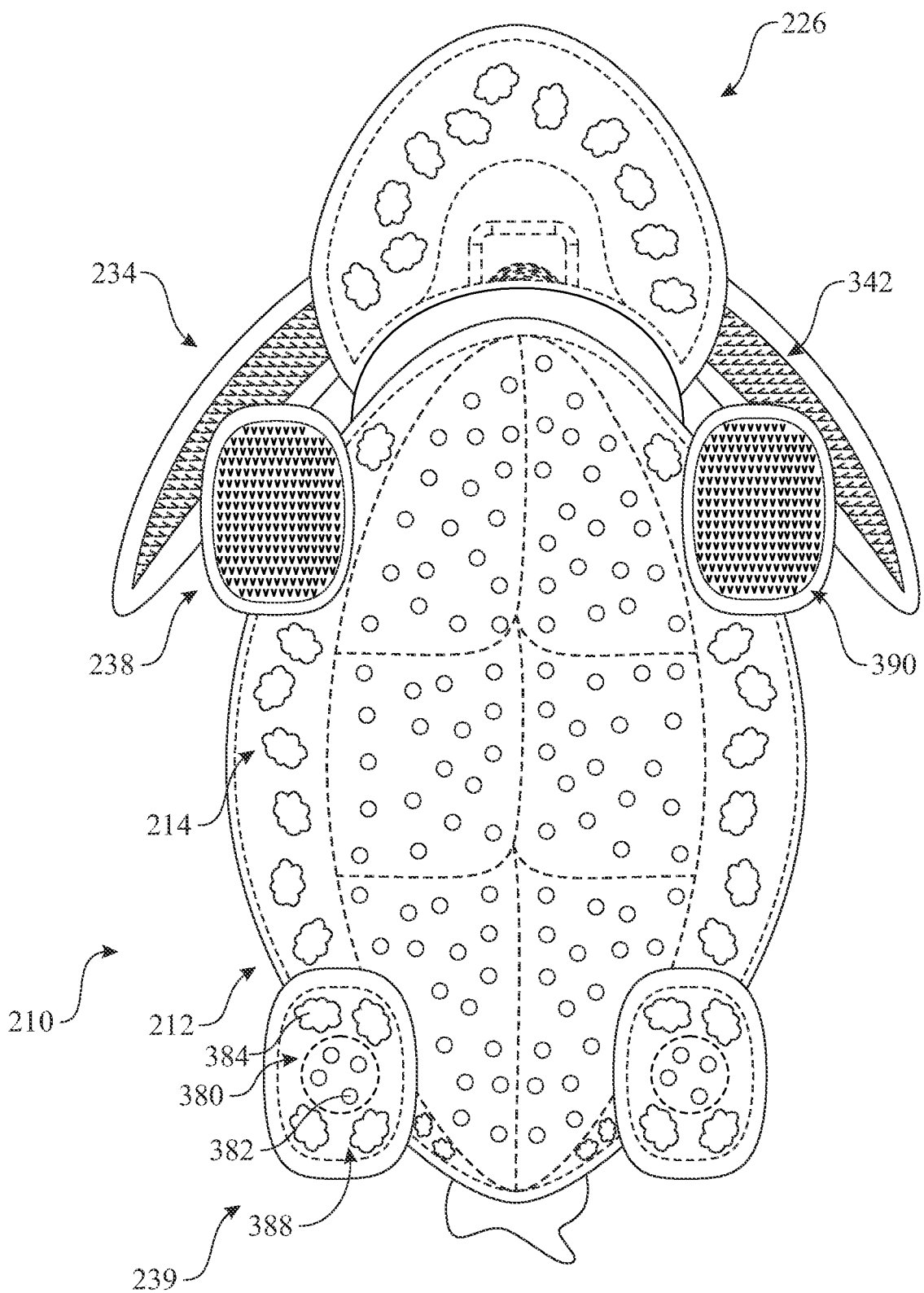
FIG. 8 presents a ventral-side, partial interior and partial exterior bottom view of the second embodiment of the therapeutic stuffed animal device of the present invention originally disclosed in FIG. 7, illustrating exterior features of the ears and feet and interior features of the head, body, and feet.

Referring now to FIGS. 8-10, the front and rear paws 238, 239 incorporate a respective casing 350, 372 densely filled with micros-glass beads 352 to create a stress ball function. The bead-filled casings 350, 372 are surrounded by cluster fiber fill 366, 378, respectively. More particularly, regarding the front limbs of rabbit device 200, the combination of foreleg 230 and front paw 238 is defined by a continuous lining 360 that terminates at its upper end at the portion of outer fur layer 240 belonging to belly 222. For example, the forelimb lining 360 is joined, stitched, and otherwise fastened to the torso lining 240, preventing access to the legs from the interior of body 210. The interior space of front paw 238 includes a casing 350 filled with a collection of micro-beads 352. In one form, the bead-filled, front paw casing 350 is enclosed within another casing 358 (FIG. 9) that carries and otherwise holds front paw casing 350. The space between the bead-filled casing 350 and casing 358 is filled with stuffing 354. In one form, in order to fix the location of front paw casing 350 within front foot 238 (e.g., to prevent displacement and movement of front paw casing 350), an optional partition or divider 362 is arranged in foreleg 230 to separate the front paw 238 from the upper section of foreleg 230. The inner space 364 of foreleg 230 is filled with an adequate amount of filling material 366. In an optional feature, each front paw 238 (rear paw 239) may be equipped and otherwise fitted with a removable, slip-on, sleeve-like outer covering 356. A similar construction is provided in rear paw 239. In particular, regarding the rear limbs of rabbit device 200, the combination of hindleg 232 and rear paw 239 is defined by a continuous lining 370 that terminates at its upper end at the portion of outer fur layer 240 belonging to belly 222. The interior space of rear paw 239 includes a casing 380 filled with a collection of micro-beads 382. In one form, the bead-filled, rear paw casing 380 is enclosed within another casing 388 (FIG. 8) that carries and otherwise holds rear paw casing 380. The space between the bead-filled casing 380 and enclosure casing 388 is filled with stuffing 384. The inner space 374 of hindleg 232 is filled with an adequate amount of filling material 384. The fill materials 256 (head 226 and torso 220), 354 and 366 (front paw 238 and foreleg 230), and 384 (rear paw 239 and hindleg 232) have a similar construction. The bottom side or sole of front paws 238 and rear paws 239 is preferably provided with an external textured feature or pad 390, which may have a roughened texture (e.g., Velcro) to promote a sensory integration therapy experience.

The article 200 may be equipped with various additional features to promote a therapeutic experience for the individual handling article 200. In order to promote balance, the combination of cluster fill and micro-glass beads in each limb is evenly distributed, preferably so that each foot and leg combination offers the same overall weight and weight distribution. For the user, this balance offers an attractive cradling or holding experience. Additionally, in quadruped animal configurations of article 200, the legs should be sufficiently flexible to enable the animal to occupy various positions, such as to sit back on its hind legs, and spread with two legs front and two legs behind on belly. The purpose of such flexibility is to provide equal balancing distribution on the legs. The exterior structure or outer casing of article 200 is preferably formed to provide an appealing visual stimulus. In animal configurations, it is desirable to make article 200 resemble the animal figure as much as possible. In the disclosed rabbit configuration, for example, the facial features should be as realistic as possible, such as black eyeliner around the eyes. The collar disposed about the neck may be provided in the form of a wool collar diffuser, which offers both tactile stimulation from the wool texture and an olfactory stimulation from the diffuser feature. The collar may be removable so that other versions can be used depending on the application and tailored to the individual. Various features can be implemented to accompany the audio device located in the head. The pouch holding the audio device is preferably attached to the head casing that holds the filling. The audio device is removed before article 200 is washed, using the zipper located on the back of the neck to facilitate interior access into the body. All other components of the animals will have fabrics that are machine washable and air-dry setting. The pouch holding the audio device can be drawstring or any other suitable means.

The article 200 has a variety of material specifications. In one form, for example, the casing or lining components can be implemented with a spandex-type material. This material selection supports☐ the ability of article 200 to undergo repeated resilient squeezing in the paws to create the stress ball effect, without bursting. Additionally, the lining material needs to have the ability, in combination with the cluster fill, to evenly fill around the inner weighted core to create the soft comfort. It is a preferable feature that the inner weighted casing is able to internally press against the inside of the outer fur, which can be accommodated by a suitable selection of fill material to permit such pressure communication.☐

The article 200 deploys casings or enclosures at various locations to maintain adequate, concentrated weighting and to provide balance, symmetry, and structural integrity. An inner casing in the torso includes multiple weighted chambers each containing a collection of micro-glass beads. As an optional feature, the torso may be equipped with an additional internal enclosure that contains the combination of multi-chambered weighted casing and surrounding fill material. In another optional feature, the head may be equipped with an additional internal enclosure that contains the combination of audio playback device and surrounding fill material. These additional enclosures would be distinct from the exterior structure or outer layer of article 200.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A therapeutic liftable device, comprising:
    a body having a head, a torso, and at least two limbs, the at least two limbs include a leg portion and a foot portion, in an interior space of each of the two limbs there is a partition separating the leg portion and the foot portion delimiting an interior leg space and an interior foot space;
    an outer structure defining an exterior of the body;
    a plurality of objects;
    an inner enclosure disposed in the torso and including a plurality of compartments each containing a respective portion of the objects; and
    a fill material, wherein a respective portion of the fill material is disposed in the head and wherein a respective portion of the fill material is disposed in the torso about the inner enclosure and inside of the interior leg space, and
        wherein a respective portion of the objects is disposed inside of the interior foot space of the foot portion of the body.

2. The device as recited in claim 1, further includes a removable audio playback device disposed in the head.

3. The device as recited in claim 1, wherein the body is configured in a shape of at least one of an anthropomorphic figure, an animal, a character, or a creature.

4. The device as recited in claim 1, wherein the body is configured as one of a biped and a quadruped animal figure.

5. The device as recited in claim 1, wherein each object includes a micro-glass article.

6. The device as recited in claim 1, further includes:
    a removable user-activatable audio device disposed in the head;
    an accessway defined in the outer structure and configured to enable access into an interior of the body;
    a pair of ears disposed on the head;
    a first textured feature defined in at least one side of at least one ear; and
        a second textured feature defined at a bottom side of the foot.

7. The device as recited in claim 6, wherein the accessway is located proximal a neck of the body.

8. The device as recited in claim 1, wherein the outer structure includes a first portion encompassing the head and torso and a second portion distinct from the first portion and encompassing the at least two limbs.

9. The device as recited in claim 1, further includes a clearance gap between the inner enclosure and the outer structure.

10. A therapeutic liftable device, comprising:
    an exterior portion and an interior portion defined by the exterior portion;
    the exterior portion defining a body having a head, a torso, and at least two limbs;
    an inner enclosure disposed in the interior portion at the torso and including a plurality of contiguous weighted chambers; and
    a fill material, wherein a respective portion of the fill material is disposed in the head and wherein a respective portion of the fill material is disposed in the torso about the inner enclosure;
    each limb respectively includes:
        a leg and a foot, the leg and the foot including an interior space that includes a partition wall separating the interior space and delimiting an interior leg space and an interior foot space,
        the foot including a foot combination comprising a weighted container and a respective portion of the fill material disposed about the weighted container inside of the interior foot space, and
        wherein a respective portion of the fill material is disposed in the interior leg space.

11. The device as recited in claim 10, wherein each limb further includes an enclosure containing the foot combination.

12. The device as recited in claim 10, further includes:
    a plurality of objects;
    wherein each weighted chamber of the inner enclosure contains a respective portion of the objects; and
    wherein the weighted container of the foot combination of each foot contains a respective portion of the objects.

13. The device as recited in claim 12, wherein each object includes a micro-glass article.

14. The device as recited in claim 10, further includes:
    a removable audio device disposed in the head;
    a closeable opening located proximal a neck of the body and configured to enable access into the interior portion of the body;

a pair of ears disposed on the head;
a first textured feature defined in at least one side of at least one ear; and
a second textured feature defined at a bottom side of the foot of at least one limb.

15. A therapeutic liftable device, comprising:
a body defining an exterior portion and an interior portion, the body including a head, a torso, and at least two limbs;
a removable audio device disposed in the head;
at least one ear disposed on the head;
a first textured feature defined in at least one side of at least one ear;
a plurality of objects;
an inner enclosure disposed in the interior portion at the torso and including a plurality of compartments each containing a respective portion of the objects;
a fill material, wherein a respective portion of the fill material is disposed in the head and wherein a respective portion of the fill material is disposed in the torso about the inner enclosure;
at least one of the at least two limbs respectively includes:
a leg and a foot, the leg and the foot including an interior space that includes a partition wall separating the interior space and delimiting an interior leg space and an interior foot space,
the foot including a foot combination,
the foot combination comprising a container within the interior foot space containing a respective portion of the objects and further comprising a respective portion of the fill material disposed about the container,
wherein a respective portion of the fill material is disposed in the interior leg space, and
a second textured feature defined at a bottom side of the foot.

16. The device as recited in claim 15, wherein the at least one of the at least two limbs respectively includes an enclosure containing the foot combination.

17. The device as recited in claim 15, further includes a closeable opening located proximal a neck of the body and configured to enable access into the interior portion of the body.

18. The device as recited in claim 15, wherein each object includes a micro-glass article.

* * * * *